Sept. 5, 1961 R. J. MASEK Plant Pat. 2,088
ROSE PLANT
Filed Nov. 15, 1960
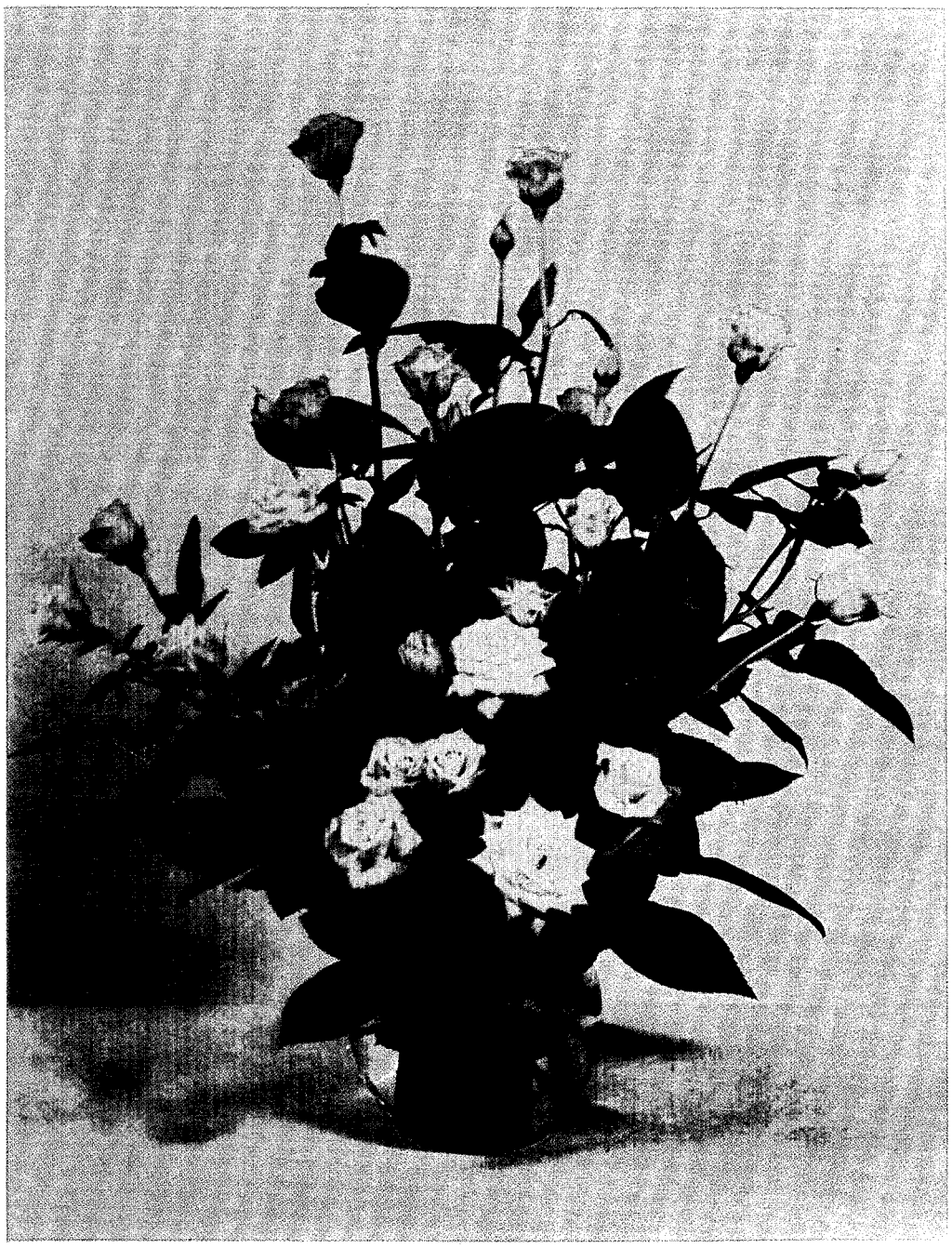
INVENTOR
Raymond J. Masek
BY Robb & Robb
ATTORNEYS United States Patent Office Plant Pat. 2,088
Patented Sept. 5, 1961

2,088
ROSE PLANT

Raymond J. Masek, 10240 E. Big Ben Road, Kirkwood, Mo.

Filed Nov. 15, 1960, Ser. No. 69,533
1 Claim. (Cl. 47—61)

The present invention relates to a new and distinct variety of rose plant of the polyantha class, which was discovered by me as a sport of the variety known as "Patty's Pink" (Plant Patent No. 1,860).

At the time of my original discovery of this new sport, I was engaged in commercially growing plants of the variety called "Patty's Pink" in my greenhouses at Kirkwood, Missouri. While inspecting these plants, my attention was attracted to one plant which bore flowers of a distinct and attractive red color, instead of the normal pink colored blooms customarily borne by the parent variety. Upon close examination of this plant, I found that one of the plants of the variety "Patty's Pink" had sported and I thereupon took steps to carefully preserve the sport, keep it under observation and to later asexually reproduce the same. These observations and asexual reproductions as performed by me by budding at Kirkwood, Missouri, and also as budded on my behalf at Carlton, Oregon, conclusively established that the red color of the blooms of the new sport was fixed and established and capable of being transmitted through succeeding propagations.

In addition to the distinctive red color of the blooms, my new sport is endowed with the following unique and desirable combination of characteristics which are outstanding therein and which distinguish it from its parent, as well as from all other varieties of which I am aware:

(1) A prolific, strong and long-stemmed bush habit;

(2) Exceptional top quality of the flowers, which makes practically all flowers of saleable quality, and which is particularly desirable from a commercial standpoint;

(3) Large size of both the flower buds and open flowers;

(4) Very stiff and well-proportioned flower necks on which the flower heads are borne;

(5) A distinctive, attractive and uniform Rose Red general color tonality of the flowers, accompanied by prolonged uniform color retention thereof throughout the life of the flowers;

(6) Very hard petal texture, with the petals being retained without dropping throughout the life of the flowers; and (7) Exceptionally long keeping qualities of the flowers, ranging from 10 to 21 days.

The accompanying drawing shows typical specimens of the vegetative growth and flowers of my new variety in different stages of development and as depicted in color as nearly true as it is reasonably possible to make the same in a color illustration of this character.

The following is a detailed description of my new variety with color terminology in accordance with the British Horticultural Colour Chart, except where general color terms of ordinary dictionary significance are obvious:

Type: Hardy; bush; greenhouse and outdoor; sport; for cut flowers and for garden decoration.
Class: Polyantha.
Parentage: Sport of "Patty's Pink."
Propagation: Holds its distinguishing characteristics through succeeding propagations by budding.

*Flower*

Locality where grown and observed: Kirkwood, Missouri.
Continuity: Continuous.

Fragrance: Moderate. Nature—tea.
Flowers borne: Singly; on long, strong stems.
Quantity of bloom: Free and abundant, both outdoors and in greenhouse.
Bud.
*Peduncle.*—Medium length; erect; stiff; smooth.
*Before calyx breaks.*—Size—from medium to large. Form—long; pointed; globular; with foliaceous appendages on the surface of the bud; without foliaceous parts extending beyond the tip of the bud. Color—Tyrian Rose, Plate 24.
*As calyx breaks.*—Color—Rose Red, Plate 724.
*As first petal opens.*—Size—medium. Form—long; pointed; globular. Color: outside—Rose Red, Plate 724; inside—Rose Red, Plate 724.
*Opening.*—Opens up well; is retarded in opening by cold weather.
Bloom:
*Size (when fully open).*—Medium; from 2¼ inches to 3½ inches.
*Petalage.*—Double (more petals, but the stamens not hidden); from 40 to 45 petals; arranged regularly.
*Form.*—Full and high-centered at first, but becoming flat; petals being at first tightly rolled inward, but later becoming very loosely cupped outward at maturity.
Petals:
*Texture.*—Thick; leathery.
*Appearance.*—Inside—satiny. Outside—satiny.
*Shape.*—Outside petals—obovate, with two notches. Intermediate petals—obovate, with two notches. Inside petals—obovate, with two notches.

This description of a newly opened flower was made from a rose grown in a greenhouse during the month of October at Kirkwood, Missouri:

*Color.*—Outer petal: outside surface—Rose Red, Plate 724; inside surface—Rose Red, Plate 724. Intermediate petal: outside surface—Rose Red, Plate 724; inside surface—Rose Red, Plate 724. Inner petal: outside surface—Rose Red, Plate 724; inside surface—Rose Red, Plate 724.

This description was made from a rose that was open for three days in a greenhouse during the month of October at Kirkwood, Missouri:

*Color.*—Outer petal: outside surface—Rose Red, Plate 724; inside surface—Rose Red, Plate 724. Inner petal: outside surface—Rose Red, Plate 724; inside surface—Rose Red, Plate 724.
*General color effect.*—Newly opened flower—Rose Red, Plate 724. 3 days open—Rose Red, Plate 724.
*Behavior.*—Persist; cold weather retards opening, while hot weather accelerates opening.
*Flower longevity.*—On bush in garden—from 10 to 14 days in October. Cut roses grown outdoors and kept at living-room temperatures—from 10 to 14 days in October. Cut roses grown in greenhouse and kept at livingroom temperature—from 12 to 21 days in October.

*Reproductive organs*

Stamens: Many; arranged irregularly about pistils. Color—from gold to bright yellow.
Filaments: Medium length; many with anthers.
Anthers: Medium size; open at various times.
Pollen: Moderate abundance.
Pistils: Few.
Styles: Uneven; medium length; heavy; bunched.
Ovaries: All enclosed in calyx.
Hips: Globular; moderately smooth; walls thick and fleshy.

Sepals: Permanent; long; spear-shaped; curled. Color—Spinach Green, Plate 0960/2.
Seeds: Few; medium size.

*Plant*

Foliage:

*Leaves.*—Compound of 5 leaflets; normal abundance; medium size; moderately heavy; leathery; glossy.

*Leaflets.*—Shape—from oval to elliptical, with apex acute. Base—obtuse. Margin—serrate.

*Color.*—Mature: upper surface—Spinach Green, Plate 0960; glossy and shiny; under surface—Spinach Green, Plate 0960/2. Young: upper surface—outer marginal half Rhodonite Red, Plate 0022, merging into Sap Green, Plate 62 which extends to center of main vein; shiny; under surface—outer marginal half Rhodonite Red, Plate 0022/2, merging into Sap Green, Plate 62/2; dull.

*Rachis (the supporting stem of the compound leaf).* — Heavy. Upper side — smooth. Under side—sparsely thorny.

*Stipules.*—Moderately long; medium width; with moderately long points turning out at an angle of more or less than 45°.

*Disease and insect resistance.*—Good resistance to mildew, and exceptionally good resistance to red spider mite, as determined by comparison with other varieties grown under comparable cultural conditions at Kirkwood, Missouri.

Growth:

*Habit.*—Bushy; much-branched.

*Growth.*—Vigorous.

*Canes.*—Medium heaviness.

*Main stems.*—Color—bright green. Thorns—few; almost straight; with long, narrow base. Prickles—none. Hairs—none.

*Branches.*—Color — bright green. Thorns — few; long; almost straight; with long, narrow base. Prickles—none. Hairs—none.

*New shoots.*—Color — bright red. Thorns — few; long; almost straight. Prickles—none. Hairs—none.

I claim:

A new and distinct variety of rose plant of the polyantha class, substantially as herein shown and described, characterized particularly as to novelty by the unique combination of a prolific, strong and long-stemmed bush habit, the exceptional top quality of practically all flowers, the large size of both the flower buds and open flowers, the very stiff and well-proportioned flower necks on which the flower heads are borne, a distinctive, attractive and uniform Rose Red general color tonality of the flowers and attending prolonged uniform color retention thereof through out their life, a very hard petal texture, with attendant prolonged retention of the petals without dropping throughout the life of the flowers, and the exceptionally long keeping qualities of the flowers.

No references cited.